(12) United States Patent
Sato et al.

(10) Patent No.: US 8,687,183 B2
(45) Date of Patent: Apr. 1, 2014

(54) IMPRINT APPARATUS, DETECTION METHOD, ARTICLE MANUFACTURING METHOD, AND FOREIGN PARTICLE DETECTION APPARATUS

(75) Inventors: Hiroshi Sato, Utsunomiya (JP); Takanori Uemura, Utsunomiya (JP)

(73) Assignee: Canon Kabushiki Kaisha (JP)

( * ) Notice: Subject to any disclaimer, the term of this patent is extended or adjusted under 35 U.S.C. 154(b) by 78 days.

(21) Appl. No.: 13/354,430

(22) Filed: Jan. 20, 2012

(65) Prior Publication Data

US 2012/0188536 A1 Jul. 26, 2012

(30) Foreign Application Priority Data

Jan. 26, 2011 (JP) ................................. 2011-014383
Dec. 26, 2011 (JP) ................................. 2011-284462

(51) Int. Cl.
*G01N 21/00* (2006.01)
(52) U.S. Cl.
USPC ....................................................... 356/237.4
(58) Field of Classification Search
USPC .................... 356/237.4, 73; 216/48; 264/40.1
See application file for complete search history.

(56) References Cited

U.S. PATENT DOCUMENTS

| 6,774,987 | B2 * | 8/2004 | Komatsu et al. | 356/73 |
| 2010/0072647 | A1 * | 3/2010 | Tokue et al. | 264/40.1 |
| 2010/0237045 | A1 * | 9/2010 | Koshiba et al. | 216/48 |

FOREIGN PATENT DOCUMENTS

JP 7-43312 A 2/1995

* cited by examiner

*Primary Examiner* — Tarifur Chowdhury
*Assistant Examiner* — Jamil Ahmed
(74) *Attorney, Agent, or Firm* — Rossi, Kimms & McDowell LLP (57) ABSTRACT

The present invention provides an imprint apparatus for performing an imprint process of transferring a pattern onto a substrate by curing a resin on the substrate while the resin is in contact with a mold, and removing the mold from the cured resin, including a detection unit configured to detect a foreign particle existing on the substrate, wherein the detection unit includes an obtaining unit configured to irradiate a surface of the substrate with light, and obtain light from the surface of the substrate, and a specification unit configured to specify a shot region where a foreign particle existing on the substrate is positioned, based on the light obtained by the obtaining unit.

11 Claims, 6 Drawing Sheets

IMPRINT APPARATUS, DETECTION METHOD, ARTICLE MANUFACTURING METHOD, AND FOREIGN PARTICLE DETECTION APPARATUS

BACKGROUND OF THE INVENTION

1. Field of the Invention

The present invention relates to an imprint apparatus, detection method, article manufacturing method, and foreign particle detection apparatus.

2. Description of the Related Art

An exposure apparatus generally has no function of detecting foreign particles existing on a substrate such as a wafer. This is so because an exposure apparatus uses an optical transfer technique, so even if a foreign particle exists on a substrate, only a shot region where the foreign particle exists becomes defective, and there is no influence on other regions where no foreign particle exists. However, a technique of detecting foreign particles existing on a substrate before it is loaded into an exposure apparatus, that is, detecting foreign particles existing on a substrate outside an exposure apparatus is known. On the other hand, if a foreign particle exists on a reticle (mask), all shot regions on a substrate onto which a pattern of the reticle is to be transferred is affected (that is, all the shot regions become defective). Accordingly, an exposure apparatus has a function of detecting foreign particles existing on a reticle (or pellicle) (see Japanese Patent Laid-Open No. 7-43312).

Also, an imprint apparatus has recently attracted attention as a lithography apparatus using the imprint technique. The imprint apparatus cures a resin on a substrate while pressing a template (mold) having fine patterns against the resin, and transfers the patterns onto the substrate by removing the mold from the cured resin.

In this imprint apparatus, however, if a foreign particle exists on a substrate, the foreign particle is sandwiched between the mold and the substrate when the mold is pressed against the substrate, and this may break the patterns of the mold. To prevent this, it is possible to detect foreign particles existing on a substrate outside the imprint apparatus by using the above-described technique, and load the substrate from which the foreign particles are removed in accordance with the detection results into the imprint apparatus. In this case, however, a foreign particle may adhere on the substrate while it is loaded into the imprint apparatus.

SUMMARY OF THE INVENTION

The present invention provides a technique capable of detecting foreign particles existing on a substrate inside an apparatus.

According to one aspect of the present invention, there is provided an imprint apparatus for performing an imprint process of transferring a pattern onto a substrate by curing a resin on the substrate while the resin is in contact with a mold, and removing the mold from the cured resin, including a detection unit configured to detect a foreign particle existing on the substrate, wherein the detection unit includes an obtaining unit configured to irradiate a surface of the substrate with light, and obtain light from the surface of the substrate, and a specification unit configured to specify a shot region where a foreign particle existing on the substrate is positioned, based on the light obtained by the obtaining unit, the light includes light from a plurality of marks or a plurality of patterns on the substrate, and light from a foreign particle existing on the substrate, and the specification unit specifies a layout of a plurality of shot regions on the substrate based on the light from the plurality of marks or the plurality of patterns, and specifies a shot region where the foreign particle exists from the plurality of specified shot regions based on the light from the foreign particle.

Further aspects of the present invention will become apparent from the following description of exemplary embodiments with reference to the attached drawings.

DESCRIPTION OF THE EMBODIMENTS

Preferred embodiments of the present invention will be described below with reference to the accompanying drawings. Note that the same reference numerals denote the same members throughout the drawings, and a repetitive description thereof will not be given.

Figure 1:
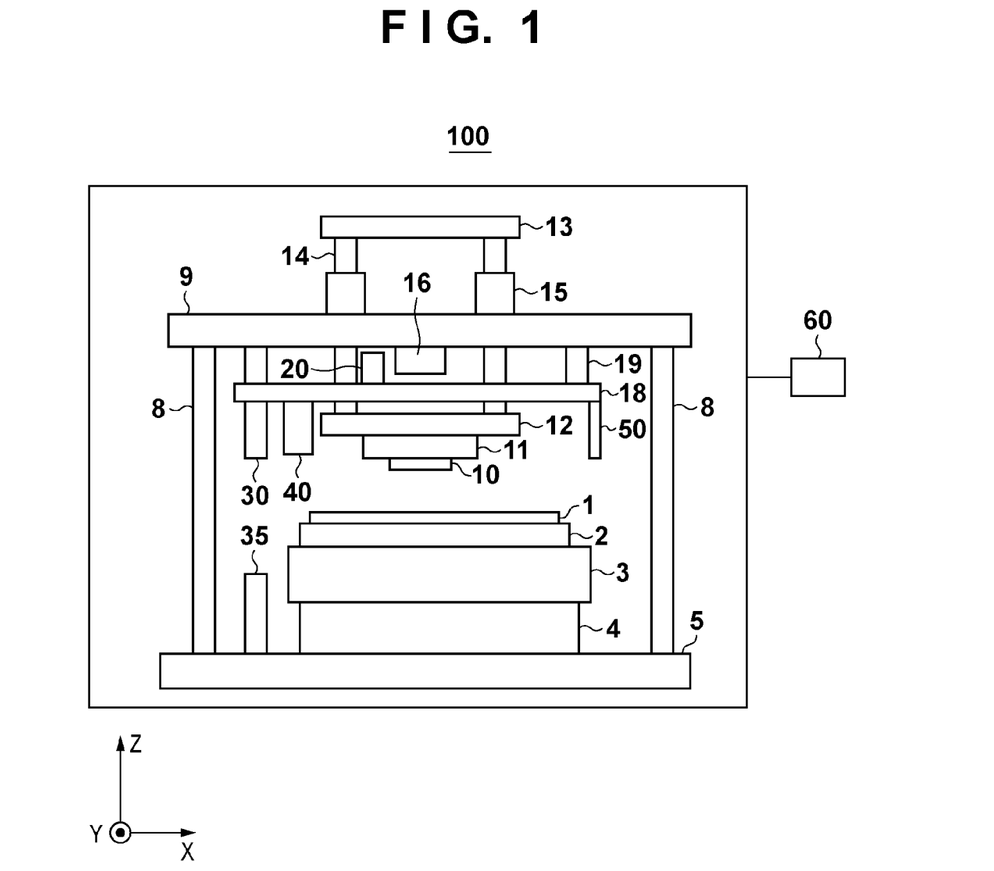
FIG. 1 is a schematic view showing the arrangement of an imprint apparatus as an aspect of the present invention.

FIG. 1 is a schematic view showing the arrangement of an imprint apparatus 100 as an aspect of the present invention. The imprint apparatus 100 performs an imprint process of forming (transferring) patterns onto a substrate by curing a resin on the substrate while the resin is in contact with a mold, and removing (releasing) the mold from the cured resin.

Referring to FIG. 1, a substrate (wafer) 1 is loaded from outside the imprint apparatus 100 by a transport unit 35 including a transport hand, and held by a chuck 2. A fine motion stage 3 has a function of correcting the rotation of the substrate 1 around the Z-axis, a function of correcting the position of the substrate 1 in the Z-axis direction, and a function of correcting the tilt of the substrate 1. The fine motion stage 3 is placed on an X-Y stage 4 for positioning the substrate 1 in predetermined positions in the X- and Y-axis directions. Note that the fine motion stage 3 and X-Y stage 4 form a substrate stage for moving the substrate 1.

The X-Y stage 4 is placed on a base surface plate 5. A bar mirror (not shown) for reflecting light from a laser interferometer for measuring the positions of the fine motion stage 3 in the X- and Y-axis directions is attached to the fine motion stage 3.

A mold 10 has a surface on which patterns to be transferred onto the substrate 1 are formed, and is fixed to a mold chuck 11. The mold chuck 11 is placed on a mold stage 12. The mold stage 12 has a function of correcting the tilt of the mold 10 around the Z-axis. A laser interferometer supported by an alignment shelf 18 measures the positions of the mold chuck 11 in the X- and Y-axis directions.

Each of the mold chuck 11 and mold stage 12 has an opening (not shown) for passing UV light emitted from a UV light source 16 through a collimator lens. Also, the mold chuck 11 (or mold stage 12) includes a load cell for detecting the pressing force (imprint force) of the mold 10.

A guide bar plate 13 fixes one end of each of guide bars 14. Each guide bar 14 has the other end fixed to the mold stage 12, and extends through a top plate 9. Mold elevation actuators 15 are air cylinders or linear motors. The mold elevation actuators 15 drive the guide bars 14 in the Z-axis direction, thereby pressing the mold 10 held on the mold chuck 11 against the substrate 1, or separating the mold 10 from the substrate 1. The alignment shelf 18 is suspended from the top plate 9 by struts 19. The guide bars 14 extend through the alignment shelf 18. Also, the alignment shelf 18 includes a height measurement system (not shown) for measuring the height (flatness) of the substrate 1 held on the chuck 2 by using, e.g., the obliquely incident image shift method.

A TTM (Through The Mold) alignment scope 20 for mold alignment includes an optical system and image sensing system for observing a reference mark on the substrate stage and alignment marks formed on the mold 10. The TTM alignment scope 20 measures positional differences between the substrate stage and the mold 10 in the X- and Y-axis directions. The TTM alignment scope 20 is also used when adopting a so-called, die-by-die method that measures the relative positions of the mark on a substrate and the alignment marks formed on the mold 10 for each shot, and corrects (measures) the positional difference.

A resin supply unit 30 is a dispenser head including a nozzle for dropping a liquid photocuring resin (resist) on the surface of the substrate 1, and has a function of supplying (applying) the resin to each of a plurality of shot regions on the substrate. The resin supply unit 30 adopts, for example, a piezo jet method or micro solenoid method, and can supply the resin by a very small volume of about 1 pL (picoliter) onto the substrate. Also, the dispenser head forming the resin supply unit 30 can be a single nozzle, and can also be a linear nozzle array including more than 100 nozzles.

An off-axis alignment (OA) scope 40 performs a global alignment process of measuring alignment marks formed in a plurality of shot regions on the substrate, and determining the position of each shot. Relative alignment of the mold 10 and substrate 1 can be performed by obtaining the positional relationship between the mold 10 and the substrate stage by the TTM alignment scope 20, and the positional relationship between the substrate stage and the substrate 1 by the OA scope 40.

A detection unit (foreign particle detection apparatus) 50 detects foreign particles existing on a substrate (that is, foreign particles adhered on the substrate 1), inside the imprint apparatus 100. As will be described later, the detection unit 50 includes an irradiation unit 502 for irradiating a substrate with light, a sensor 504 for sensing scattered light scattered on the substrate, and a specification unit 506 for specifying a shot region where a foreign particle existing on the substrate is positioned. The detection unit 50 may also include a storage unit 508 for storing layout information indicating the layout of a plurality of shot regions on a substrate.

A control unit 60 includes a CPU and memory, and controls the whole (operation) of the imprint apparatus 100. For example, the control unit 60 controls operations pertaining to the imprint process based on the detection results from the detection unit 50.

Figure 2A:
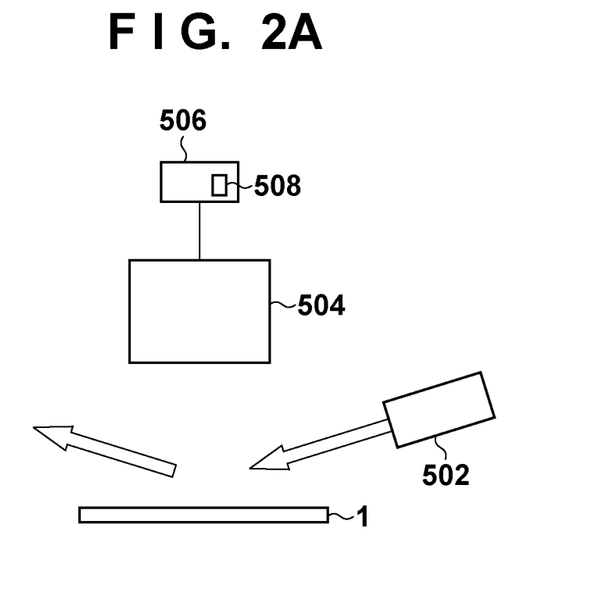
FIGS. 2A and 2B are schematic views showing the arrangement of a detection unit of the imprint apparatus shown in FIG. 1.
Figure 2B:
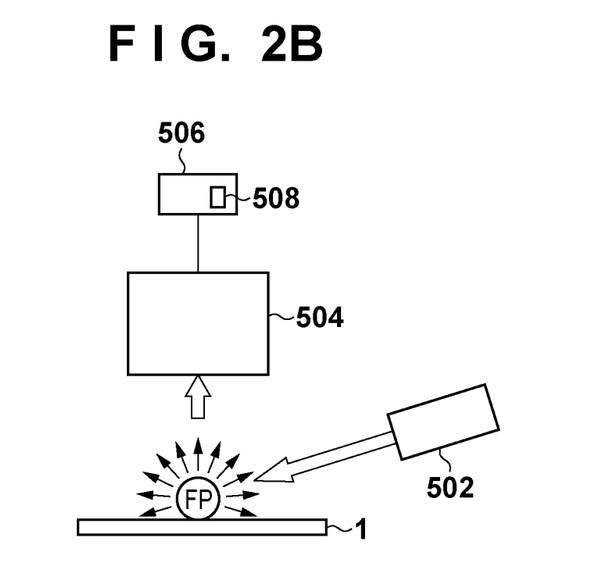

The detection of a foreign particle existing on a substrate (to be referred to as "a foreign particle detection process" hereinafter) performed by the detection unit 50 will be explained below. In the detection unit 50, the irradiation unit 502 irradiates the substrate 1 with light by the oblique incidence method (that is, to make an angle with the surface of the substrate 1), as shown in FIGS. 2A and 2B. If no foreign particle exists on the substrate 1, as shown in FIG. 2A, the light emitted from the irradiation unit 502 is regularly reflected by the surface of the substrate 1. Therefore, the light regularly reflected by the surface of the substrate 1 does not enter the sensor 504 that is not positioned on the optical axis of the irradiation unit 502. On the other hand, if a foreign particle FP exists on the substrate 1, as shown in FIG. 2B, the light emitted from the irradiation unit 502 is scattered by the foreign particle FP, and a part of the scattered light enters the sensor 504 (that is, the sensor 504 senses the light). Thus, the irradiation unit 502 and sensor 504 function as an obtaining unit for irradiating the substrate with light and obtaining the distribution of light scattered on the substrate.

Based on the scattered light distribution obtained by the irradiation unit 502 and sensor 504, the specification unit 506 determines whether the foreign particle FP exists on the substrate (that is, the presence/absence of the foreign particle FP). In the examples shown in FIGS. 2A and 2B, the specification unit 506 can determine that the foreign particle FP exists on the substrate if the sensor 504 senses the scattered light, and that no foreign particle FP exists on the substrate if the sensor 504 senses no scattered light. Note that the specification unit 506 can also specify the size of the foreign particle FP based on the intensity of the scattered light sensed by the sensor 504. This is so because the intensity of the scattered light sensed by the sensor 504 is high when the size of the foreign particle FP is large, and the intensity of the scattered light sensed by the sensor 504 is low when the size of the foreign particle FP is small.

Figure 3A:
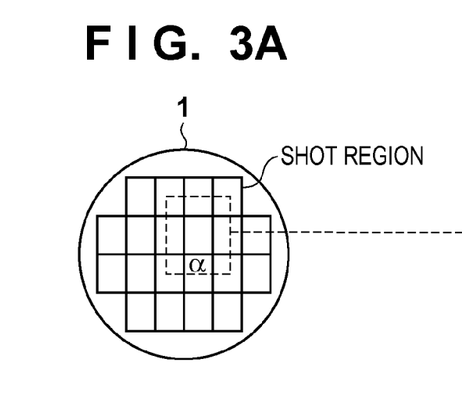
FIGS. 3A to 3D are exemplary views showing a substrate as an object of a foreign particle detection process performed by the detection unit shown in FIGS. 2A and 2B.
Figure 3B:
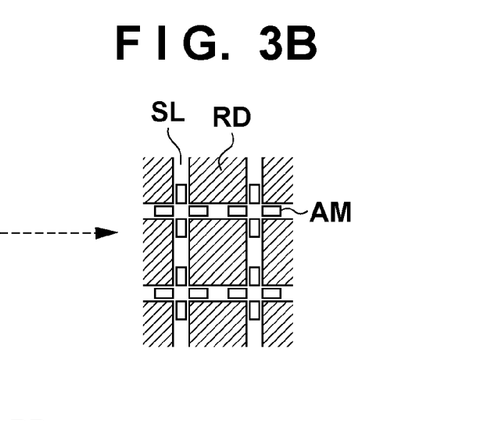

FIGS. 3A to 3D are exemplary views showing the substrate 1 (a real element wafer) as an object of the foreign particle detection process. As shown in FIG. 3A, a plurality of shot regions each having a predetermined size are laid out on the substrate 1, and an underlying pattern corresponding to this shot region layout is formed. FIG. 3B is an enlarged view of an area a including one shot region on the substrate 1 shown in FIG. 3A. As shown in FIG. 3B, one shot region includes scribe lines SL to be cut when dividing the chip, and a real element portion RD in which a pattern is formed (or a pattern is to be formed).

In the real element portion RD, a pattern for actually forming an IC or the like is formed, and this pattern is patterned by a line width of about a few ten nm. Alignment marks AM for aligning a pattern to be transferred next and the underlying pattern are formed on the scribe lines SL. The alignment marks AM are generally marks formed by a line width of about 0.5 to a few μm, and measured by the OA scope 40 and TTM alignment scope 20.

Figure 3C:
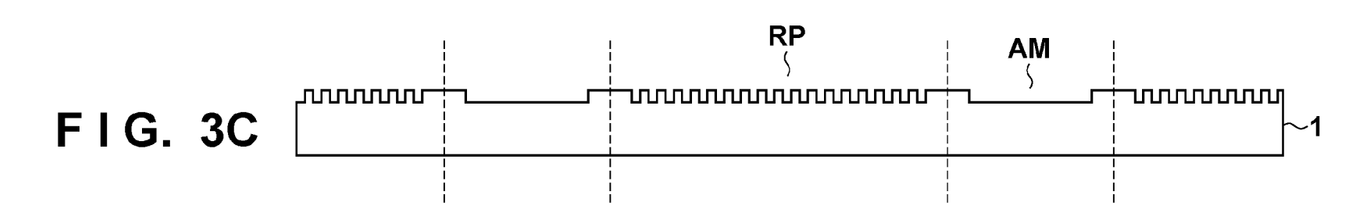

As described previously, the intensity of the scattered light sensed by the sensor 504 changes in accordance with the size of the foreign particle FP. For example, when a pattern RP in the real element portion RD is exposed to the surface as shown in FIG. 3C, a line width difference between the alignment mark AM and the pattern RP is one or more orders of magnitude. Accordingly, the sensor 504 senses a large intensity difference between scattered light scattered by the alignment mark AM and scattered light scattered by the pattern RP in the real element portion RD. This makes it possible to distinguish between the scattered light from the alignment mark AM and that from the pattern RP.

Figure 3D:
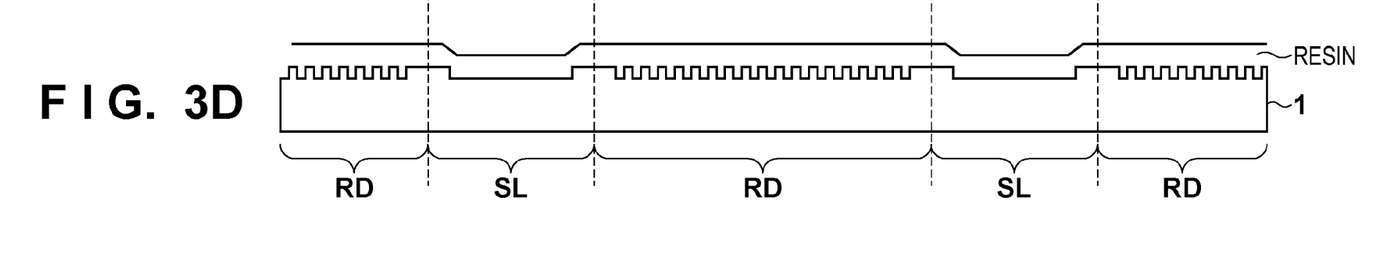

Also, when the substrate 1 is covered with a layer such as a resin as shown in FIG. 3D, the surface layer becomes uneven because the alignment mark AM has a large three-dimensional structure. However, the pattern RP in the real element portion RD has a fine three-dimensional structure, so the surface layer does not become uneven. Since the sensor 504 senses a large intensity difference, therefore, it is possible to distinguish between the scattered light from (the resin surface layer covering) the alignment mark AM and that from (the resin surface layer covering) the pattern RP in the real element portion RD.

Figure 4A:
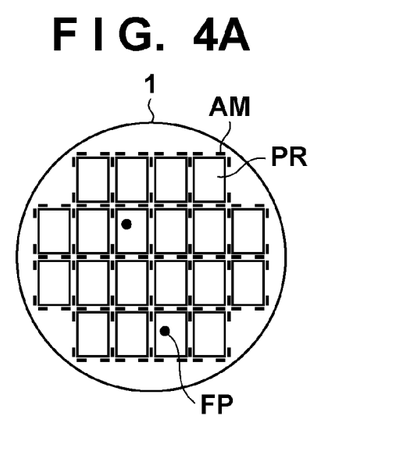
FIGS. 4A to 4D are views for explaining details of the foreign particle detection process performed by the detection unit shown in FIGS. 2A and 2B.

The foreign particle detection process performed by the detection unit 50 will be explained in detail below with reference to FIGS. 4A to 4D. FIG. 4A shows the substrate 1 including the patterns RP formed in the real element portions RD, and the alignment marks AM formed on the scribe lines SL. Note that the foreign particles FP exist on the substrate 1.

Figure 4B:
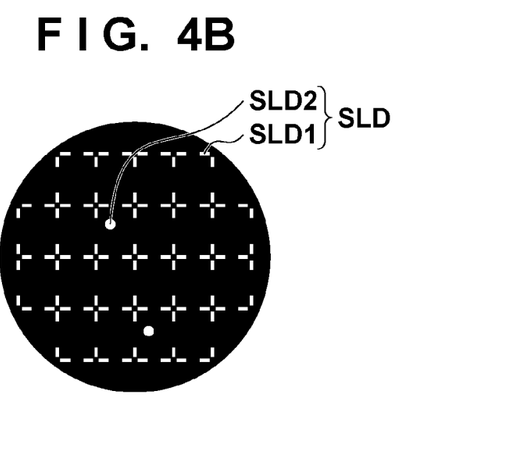

In this embodiment, the detection unit 50 performs the foreign particle detection process before an imprint process of transferring a new pattern onto (the real element portions RD of) the substrate 1 shown in FIG. 4A is performed. First, the irradiation unit 502 irradiates the substrate 1 shown in FIG. 4A with light, and the sensor 504 senses scattered light from the substrate 1. This scattered light from the substrate 1, which is sensed by the sensor 504, includes scattered light from the alignment marks AM and scattered light from the foreign particles FP, but includes almost no scattered light from the patterns RP in the real element portions RD, as described previously. As shown in FIG. 4B, therefore, a scattered light distribution SLD including a distribution SLD1 of the scattered light from the alignment marks AM and a distribution SLD2 of the scattered light from the foreign particles FP is obtained.

Figure 4C:
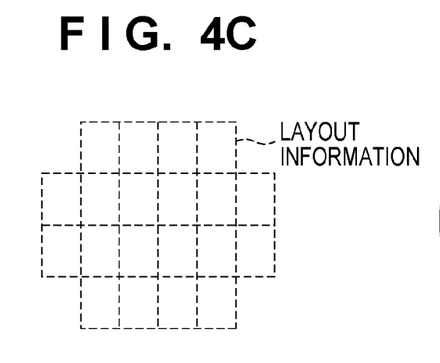
Figure 4D:
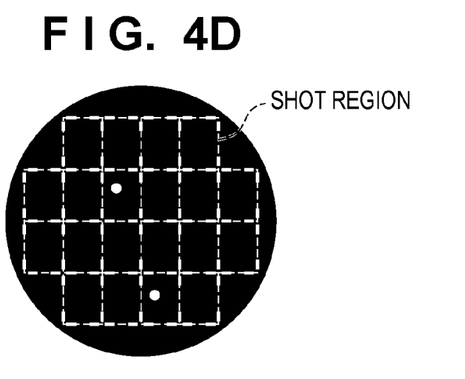

When the scattered light distribution SLD is obtained, as shown in FIG. 4C, the specification unit 506 specifies the layout of a plurality of shot regions on the substrate based on the distribution SLD1 of the scattered light from the alignment marks AM. In this processing, the specification unit 506 may also fit layout information as shown in FIG. 4D stored in the storage unit 508, on the distribution SLD1 of the scattered light from the alignment marks AM. This makes it possible to more reliably specify the layout of the plurality of shot regions on the substrate. When the layout of the plurality of shot regions on the substrate is specified, the specification unit 506 specifies shots in which the foreign particles FP exist, from the plurality of specified shots based on the distribution SLD2 of the scattered light from the foreign particles FP. The present embodiment assumed that the scattered light from the substrate 1 detected by the sensor 504 hardly include the scattered light from the real element portions RD. However, if the real element portions RD includes a characteristic pattern (for example, a large or thick pattern), it is possible to use a scattered light from the characteristic pattern in the real element portions RD instead of the scattered light from the alignment mark.

Note that when performing the foreign particle detection process, the substrate 1 may have rotated from a reference state (for example, the substrate 1 may have rotated 90°, 180°, or 270° from 0° as the reference state). In this case, if the shape of each shot region on the substrate is not square, the state in which the substrate 1 has rotated 90° or 270° from the reference state can be discriminated, but the state in which the substrate 1 has rotated 180° from the reference state cannot be discriminated. To discriminate the state in which the substrate 1 has rotated 180° from the reference state, it is only necessary to use a notch or an orientation flat (notched region) formed in the circumference of the substrate 1 and indicating the crystal direction of silicon. For example, the irradiation unit 502 irradiates the circumference of the substrate 1 with light, and the sensor 504 senses scattered light scattered by the notch or orientation flat formed in the circumference of the substrate 1. This makes it possible to discriminate the state in which the substrate 1 has rotated 180° from the reference state.

Also, in the foreign particle detection process of this embodiment, it is necessary to irradiate the entire surface of the substrate 1 with the light from the irradiation unit 502, and obtain the distribution SDL of the scattered light from the entire surface of the substrate 1 as shown in FIG. 4B. To irradiate the entire surface of the substrate 1 with the light from the irradiation unit 502, two types of methods are possible as shown in FIGS. 5A to 5D and 5E to 5H.

The first method is a method combining scanning the light from the irradiation unit 502 so as to draw a circle on the substrate 1, and scanning the light in a uniaxial direction. More specifically, as indicated by the arrow in FIG. 5A, a first position shifted in the radial direction from the central position of the substrate 1 is irradiated with the light from the irradiation unit 502, and the light is scanned so as to draw a circle on the substrate 1. Then, as indicated by the arrow in FIG. 5B, a second position shifted in the radial direction from the central position of the substrate 1 and different from the first position is irradiated with the light from the irradiation unit 502, and the light is scanned so as to draw a circle on the substrate 1. By repeating this operation, the entire surface of the substrate 1 is irradiated with the light from the irradiation unit 502 as indicated by hatched lines in FIGS. 5A to 5D, and the distribution SLD of the scattered light from the entire surface of the substrate 1 as shown in FIG. 4B can be obtained. Note that when the scanning amount of light in the radial direction of the substrate 1 is increased, the number of times of scanning of the light in the radial direction of the substrate 1 can be decreased, but the detectivity of the foreign particles FP existing on the substrate 1 decreases.

Figure 5A:
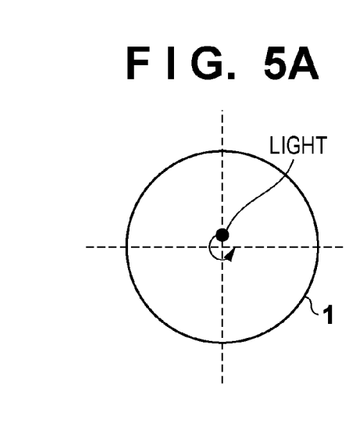
FIGS. 5A to 5H are views for explaining a method of irradiating the entire surface of a substrate with light emitted from an irradiation unit of the detection unit shown in FIGS. 2A and 2B.
Figure 5B:
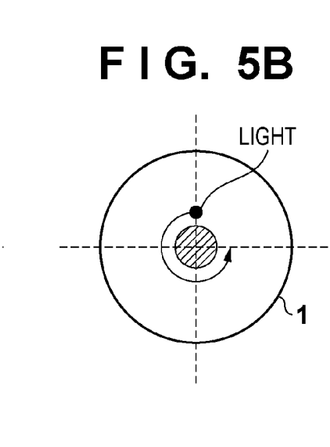
Figure 5C:
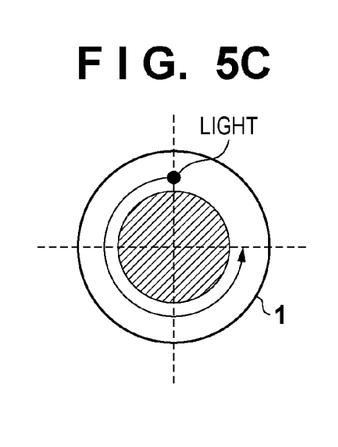
Figure 5D:
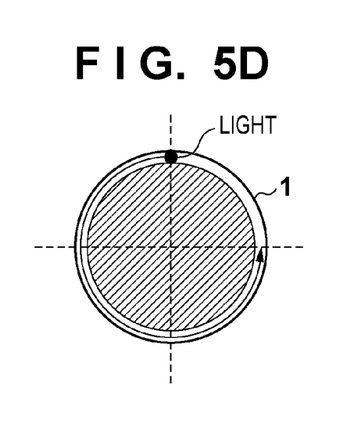
Figure 5E:
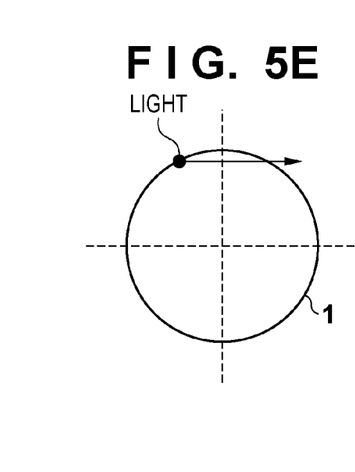
Figure 5F:
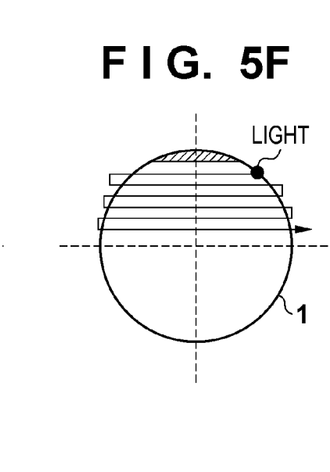
Figure 5G:
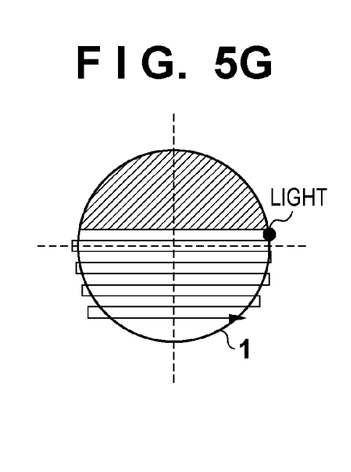
Figure 5H:
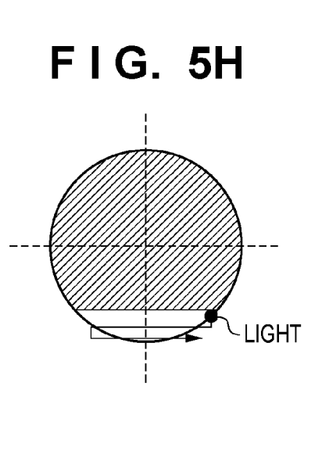

The second method is a method of scanning the light from the irradiation unit 502 in biaxial directions on the substrate 1. More specifically, as indicated by the arrow in FIG. 5E, a first end portion of the circumference of the substrate 1 is irradiated with the light from the irradiation unit 502, and the light is scanned in a first direction of the substrate 1. After the light from the irradiation unit 502 is scanned from the first end portion to a second end portion along the first direction, as shown in FIG. 5F, the light is scanned from the second end portion in a second direction perpendicular to the first direction, and positioned in a third end portion. Then, as indicated by the arrow in FIG. 5F, the light positioned in the third end portion is scanned in the direction opposite to the first direction of the substrate 1. By repeating this operation, the entire surface of the substrate 1 is irradiated with the light from the irradiation unit 502 as indicated by hatched lines in FIGS. 5E to 5H, and the distribution SLD of the scattered light from the entire surface of the substrate 1 as shown in FIG. 4B can be obtained.

In this embodiment, the entire surface of the substrate 1 is irradiated with the light from the irradiation unit 502 by scanning the light. However, the entire surface of the substrate 1 can also be irradiated with the light from the irradiation unit 502 by driving the substrate 1 relative to the light as described above, instead of scanning the light. It is also possible to combine scanning of the light from the irradiation unit 502 and driving of the substrate 1.

Figure 6:
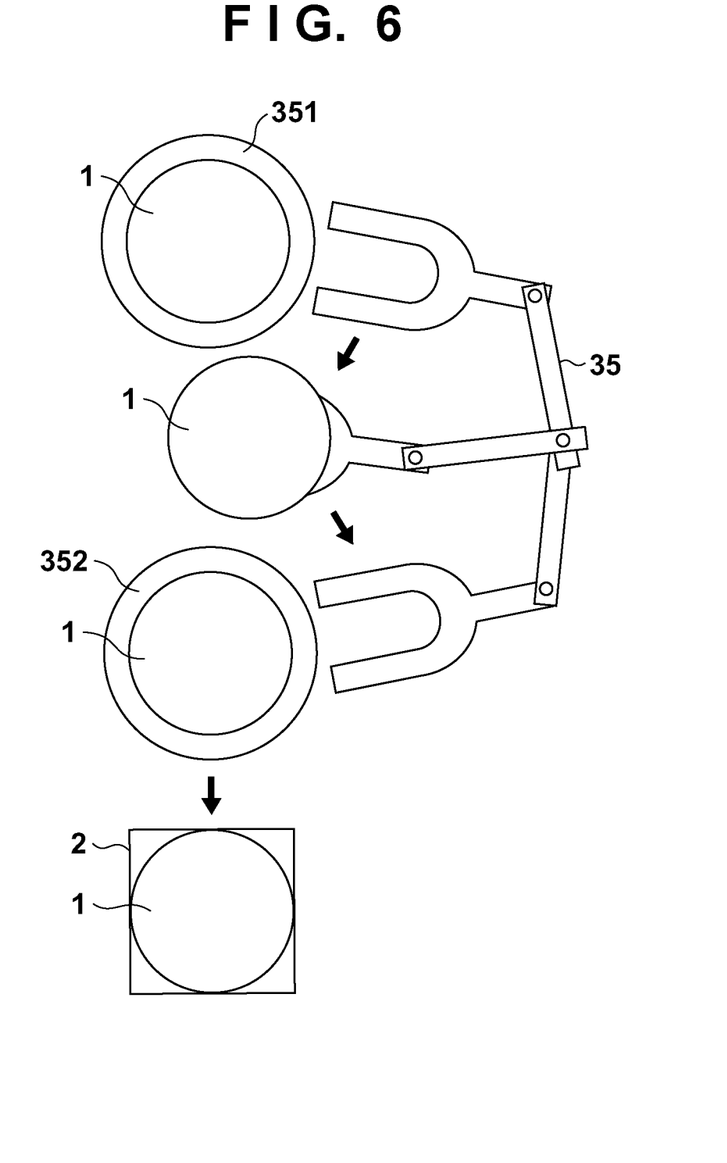
FIG. 6 is a view showing an example of substrate transport performed by a transport unit of the imprint apparatus shown in FIG. 1.

Furthermore, the foreign particle detection process of this embodiment can be performed while the transport unit 35 is transporting the substrate 1. As shown in FIG. 6, the substrate 1 loaded into the imprint apparatus 100 is placed on a temperature adjusting stage 351 for adjusting the temperature of the substrate 1 by the transport unit 35. Note that the temperature adjusting stage 351 heats or cools the substrate 1 in order to adjust the temperature of the substrate 1 (that is, the temperature of the substrate 1 outside the imprint apparatus 100) to the internal temperature of the imprint apparatus 100. Also, the transport unit 35 places the temperature-adjusted substrate 1 on a stage 352 for coarse alignment. The stage 352 pre-aligns the substrate 1 by measuring the alignment marks and the notch or orientation flat of the substrate 1. After this pre-alignment, the transport unit 35 places the substrate 1 on the chuck 2. To increase the productivity of the imprint apparatus 100, it is necessary to perform the foreign particle detection process on a substrate as a next target of the imprint process while the imprint process is performed on another substrate. Accordingly, the foreign particle detection process is performed while the transport unit 35 is transporting the substrate 1, for example, while the substrate 1 is placed on the temperature adjusting stage 351 or stage 352. It is also possible to perform the foreign particle detection process while the transport unit 35 is holding the substrate 1. Note that if the imprint apparatus 100 has sufficient productivity or has a twin-stage configuration, the foreign particle detection process may be performed after the substrate 1 is placed on the substrate stage. Note also that if the imprint apparatus 100 has the twin-stage configuration, the foreign particle detection process may be performed when a measurement station performs alignment measurement or focusing measurement.

As described above, this embodiment can detect a foreign particle existing on a substrate inside the imprint apparatus 100, and can further specify a shot region on the substrate in which the foreign particle is positioned. In accordance with this result, that is, the result of the foreign particle detection process, the control unit 60 controls operations pertaining to the imprint process as follows.

For example, if the imprint process is performed in a shot region on the substrate where a foreign particle exists, the foreign particle is sandwiched between the mold 10 and the substrate 1, and this may damage the pattern of the mold 10. Therefore, the control unit 60 performs no imprint process on a shot region found to have a foreign particle, among the plurality of shot regions on the substrate. Also, information for specifying a shot region on which no imprint process is performed must be output to a processing apparatus in the subsequent step so as not to affect processing in the subsequent step.

If, however, no imprint process is performed on a shot region found to have a foreign particle, the continuity to other shot regions in which no foreign particle exists cannot be maintained. More specifically, no resin is supplied to (applied on) a shot region found to have a foreign particle, and this may affect other shot regions in etching or the like in the subsequent step. In a case like this, the control unit 60 controls the resin supply unit 30 to supply a resin to a shot region found to have a foreign particle.

Note that the influence on the imprint process is sometimes small (for example, the patterns of the mold 10 do not break), depending on the position or size of a foreign particle in a shot region. For example, when a foreign particle exists in a region on a scribe line where no alignment mark is formed, there is probably almost no influence of the foreign particle on the imprint process. In this case, the control unit 60 can perform the imprint process even on a shot region found to have a foreign particle.

If a foreign particle exists on the substrate 1, the control unit 60 may also unload the substrate 1 outside the imprint apparatus 100 without performing any imprint process on the substrate 1. The foreign particle is removed by using a cleaning device or the like from the substrate 1 unloaded outside the imprint apparatus 100, and the substrate 1 is reloaded into the imprint apparatus 100.

As described above, the imprint apparatus 100 of this embodiment can detect foreign particles on a substrate, and perform the imprint process based on the detection results. Accordingly, the imprint apparatus 100 can prevent the breakage of the mold 10 or a pattern transfer error caused by a foreign particle on a substrate, and efficiently manufacture articles such as semiconductor devices. A manufacturing method of devices (such as a semiconductor integrated circuit element and a liquid crystal display element) as commodities includes a step of transferring (forming) a pattern on a substrate (such as a wafer, a glass plate, and a film substrate) using the imprint apparatus 100. The manufacturing method further includes a step of etching the substrate with the transferred pattern. In place of the etching step, the manufacturing method includes another processing step of processing the substrate with the transferred pattern to manufacture other commodities, such as pattern dot media (recording media) and optical elements.

Also, this embodiment has been explained by taking an example in which the distribution of scattered light from alignment marks is obtained and the layout of shot regions is specified by using this distribution. However, the present invention is not limited to the scattered light distribution, provided that it is possible to obtain light from the marks and the layout of shot regions can be specified from the obtained light.

This embodiment has been explained by taking, as an example, the detection of a foreign particle existing on a substrate loaded into an imprint apparatus. However, the present invention is not limited to the imprint apparatus, and also applicable to other lithography apparatuses such as a semiconductor exposure apparatus, a liquid crystal exposure apparatus, an exposure apparatus (EUV (Extreme Ultra Violet) exposure apparatus) using EUV light, and an electron beam exposure apparatus. For example, in the EUV exposure apparatus or electron beam exposure apparatus, an exposure light optical path or chamber is kept in a vacuum in order to reduce the absorption of the exposure light by the atmosphere. In the exposure light optical path or chamber, foreign particles are reduced by a downward air stream (a so-called down flow). However, foreign particles cannot be reduced by the down flow in a vacuum as described above, so it is necessary to more strictly detect foreign particles flowing into the exposure apparatus from the outside. This makes it useful to use the present invention to detect foreign particles on a substrate loaded into the exposure light optical path or chamber. Furthermore, a target of the foreign particle detection process is not limited to a substrate having an underlying pattern, and may also be a member having a known pattern, for example, a reticle.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent application Nos. 2011-014383 filed on Jan. 26, 2011 and 2011-284462 filed on Dec. 26, 2011, which are hereby incorporated by reference herein in their entirety.

What is claimed is:
1. An imprint apparatus for performing an imprint process of transferring a pattern onto a substrate by curing a resin on the substrate while the resin is in contact with a mold, and removing the mold from the cured resin, comprising
a detection unit configured to detect a foreign particle existing on the substrate,
wherein the detection unit comprises:
an obtaining unit configured to irradiate a surface of the substrate with light, and obtain light from the surface of the substrate; and
a specification unit configured to specify a shot region where a foreign particle existing on the substrate is positioned, based on the light obtained by the obtaining unit,
the light includes light from a plurality of marks or a plurality of patterns on the substrate, and light from a foreign particle existing on the substrate, and
the specification unit specifies a layout of a plurality of shot regions on the substrate based on the light from the plurality of marks or the plurality of patterns, and specifies a shot region where the foreign particle exists from the plurality of specified shot regions based on the light from the foreign particle.

2. The apparatus according to claim 1, wherein
the detection unit comprises a storage unit configured to store layout information indicating the layout of the plurality of short regions on the substrate, and
the specification unit specifies the layout of the plurality of shot regions on the substrate by fitting the layout information stored in the storage unit on a distribution of the light from the plurality of marks or the plurality of patterns.

3. The apparatus according to claim 1, wherein the marks are formed on scribe lines of the plurality of shot regions on the substrate.

4. The apparatus according to claim 1, wherein the marks include an alignment mark.

5. The apparatus according to claim 1, further comprising a control unit configured to control the imprint process based on a detection result from the detection unit,
wherein the control unit does not perform the imprint process on a shot region found to have the foreign particle by the specification unit, among the plurality of shot regions on the substrate.

6. The apparatus according to claim 5, further comprising a supply unit configured to supply a resin to each of the plurality of shot regions on the substrate when performing the imprint process,
wherein the control unit controls the supply unit to supply the resin to the shot region found to have the foreign particle by the specification unit.

7. The apparatus according to claim 1, wherein the obtaining unit is configured to detect a rotational angle of the substrate by irradiating a circumference of the substrate with light and obtaining light from the circumference.

8. The apparatus according to claim 1, further comprising a substrate stage configured to hold the substrate when transferring the pattern,
wherein the detection unit is configured to detect a foreign particle on a substrate onto which the pattern is to be transferred, while the substrate is transported to the substrate stage.

9. A detection method of detecting a foreign particle existing on a substrate inside a lithography apparatus for transferring a pattern onto the substrate, comprising:
an obtaining step of irradiating a surface of the substrate with light, and obtaining light from the surface of the substrate; and
a specification step of specifying a shot region where a foreign particle existing on the substrate is positioned, based on the light obtained in the obtaining step,
wherein the light includes light from a plurality of marks or a plurality of patterns on the substrate, and light from a foreign particle existing on the substrate, and
in the specification step, a layout of a plurality of shot regions on the substrate is specified based on the light from the plurality of marks or the plurality of patterns, and a shot region where the foreign particle exists is specified from the plurality of specified shot regions based on the light from the foreign particle.

10. A manufacturing method of commodities comprising:
a step of using an imprint apparatus to form a pattern on a substrate; and
a step of processing the substrate with the pattern,
wherein the imprint apparatus, for performing an imprint process of transferring a pattern onto the substrate by curing a resin on the substrate while the resin is in contact with a mold, and removing the mold from the cured resin, includes
a detection unit configured to detect a foreign particle existing on the substrate,
wherein the detection unit comprises:
an obtaining unit configured to irradiate a surface of the substrate with light, and obtain light from the surface of the substrate; and
a specification unit configured to specify a shot region where a foreign particle existing on the substrate is positioned, based on the light obtained by the obtaining unit,
the light includes light from a plurality of marks or a plurality of patterns on the substrate, and light from a foreign particle existing on the substrate, and
the specification unit specifies a layout of a plurality of shot regions on the substrate based on the light from the plurality of marks or the plurality of patterns, and specifies a shot region where the foreign particle exists from the plurality of specified shot regions based on the light from the foreign particle.

11. A foreign particle detection apparatus for detecting a foreign particle existing on a substrate including a plurality of shot regions, comprising
a detection unit configured to detect a foreign particle existing on the substrate,
wherein the detection unit comprises:
an obtaining unit configured to irradiate a surface of the substrate with light, and obtain a distribution of light from the surface of the substrate; and
a specification unit configured to specify a shot region where a foreign particle existing on the substrate exists, based on the light obtained by the obtaining unit,
the light includes light from a plurality of marks or a plurality of patterns on the substrate, and light from a foreign particle existing on the substrate, and
the specification unit specifies a layout of a plurality of shot regions on the substrate based on the light from the plurality of marks or the plurality of patterns, and specifies a shot region where the foreign particle exists from the plurality of specified shot regions based on the light from the foreign particle.

* * * * *